United States Patent
den Heijer et al.

(10) Patent No.: US 11,241,558 B2
(45) Date of Patent: Feb. 8, 2022

(54) TRAPPING CATHETER AND KIT AND METHOD FOR PREPARING A TRAPPING CATHETER

(71) Applicant: IMDS R&D B.V., Roden (NL)

(72) Inventors: Peter den Heijer, Breda (NL); Edwin Alexander Schulting, Haren (NL)

(73) Assignee: IMDS R & D B.V., Roden (NL)

( * ) Notice: Subject to any disclaimer, the term of this patent is extended or adjusted under 35 U.S.C. 154(b) by 342 days.

(21) Appl. No.: 16/334,854

(22) PCT Filed: Sep. 20, 2017

(86) PCT No.: PCT/NL2017/050620
§ 371 (c)(1),
(2) Date: Mar. 20, 2019

(87) PCT Pub. No.: WO2018/056807
PCT Pub. Date: Mar. 29, 2018

(65) Prior Publication Data
US 2020/0016372 A1 Jan. 16, 2020

(30) Foreign Application Priority Data
Sep. 20, 2016 (EP) .................................. 16189746

(51) Int. Cl.
*A61M 25/01* (2006.01)
*A61M 39/10* (2006.01)
(Continued)

(52) U.S. Cl.
CPC ........ *A61M 25/0169* (2013.01); *A61M 39/10* (2013.01); *A61M 2025/0183* (2013.01);
(Continued)

(58) Field of Classification Search
CPC .......... A61M 25/0169; A61M 25/0172; A61M 25/1061; A61M 25/1027; A61M 25/1029;
(Continued)

(56) References Cited

U.S. PATENT DOCUMENTS

| 5,395,389 A | 3/1995 | Patel |
| 5,776,111 A * | 7/1998 | Tesio .................... A61M 25/02 604/174 |

(Continued)

FOREIGN PATENT DOCUMENTS

| EP | 0415332 A1 | 3/1991 |
| EP | 0718004 A2 | 6/1996 |

(Continued)

*Primary Examiner* — James D Ponton
(74) *Attorney, Agent, or Firm* — Hoffmann & Baron LLP

(57) ABSTRACT

Trapping catheter and kit and method for preparing a trapping catheter A trapping catheter (10) for insertion into a guide catheter assembly (3) comprises a balloon (22) and a trapping catheter body (23) bounding an inflation lumen (24) extending longitudinally within the trapping balloon catheter. The inflation lumen has a distal end opening (25) into an internal space bounded by the balloon. The trapping catheter body is provided with a stopper (26) for abutting against an abutment (27) at a proximal end (27) of the guide catheter assembly so as to determine a maximum insertion depth of the trapping catheter into the guide catheter. A kit and method for preparing a trapping catheter prior to insertion into a guide catheter is also described.

10 Claims, 3 Drawing Sheets

(51) Int. Cl.
*A61M 25/06* (2006.01)
*A61M 25/10* (2013.01)

(52) U.S. Cl.
CPC ............... *A61M 2025/0681* (2013.01); *A61M 2025/1061* (2013.01)

(58) Field of Classification Search
CPC ...... A61M 25/1038; A61M 2025/0183; A61M 2025/0681; A61M 2025/1031; A61M 39/10; A61M 25/10
See application file for complete search history.

(56) References Cited

U.S. PATENT DOCUMENTS

| | | | | |
|---|---|---|---|---|
| 6,299,628 | B1* | 10/2001 | Harrison | A61M 25/0105 606/194 |
| 2007/0282302 | A1* | 12/2007 | Wachsman | A61M 25/104 604/509 |
| 2008/0154153 | A1* | 6/2008 | Heuser | A61M 25/09041 600/585 |
| 2010/0057045 | A1 | 3/2010 | Albritton, IV et al. | |
| 2011/0004057 | A1 | 1/2011 | Goldfarb et al. | |
| 2011/0034828 | A1 | 2/2011 | Holmin et al. | |
| 2014/0276432 | A1* | 9/2014 | Bierman | A61B 17/3498 604/164.1 |

FOREIGN PATENT DOCUMENTS

| | | |
|---|---|---|
| JP | 2012135379 A | 7/2012 |
| JP | 2013116329 A | 6/2013 |
| JP | 2014079351 A | 5/2014 |
| JP | 2014147800 A | 8/2014 |
| JP | 2005329062 A | 12/2015 |
| JP | 2015534855 A | 12/2015 |
| JP | 2016522069 A | 7/2016 |
| WO | 2008/013441 A1 | 1/2008 |
| WO | 2012/096816 A1 | 7/2012 |
| WO | 2014072977 A1 | 5/2014 |
| WO | 2014204954 A | 12/2014 |
| WO | 2015/153599 A1 | 10/2015 |
| WO | 2016/164682 A1 | 10/2016 |

* cited by examiner

TRAPPING CATHETER AND KIT AND METHOD FOR PREPARING A TRAPPING CATHETER

This application claims priority from International Application No. PCT/NL2017/050620, filed on Sep. 20, 2017, which claims priority from International patent application number EP 16189746.7, filed on Sep. 20, 2016, both of which are incorporated herein in their entirety.

FIELD AND BACKGROUND OF THE INVENTION

The invention relates to a trapping catheter for maintaining an elongated device, such as a guidewire, in a position in a guide catheter, to a kit for preparing such a trapping catheter and to a method for preparing a trapping catheter prior to insertion into a guide catheter.

Most dilatation catheters used in angioplasty have an inflatable balloon at the distal end thereof. Using fluoroscopy for following the progress of the catheter, the catheter is advanced through the vascular system until the balloon is positioned across a stenosis to be treated. The balloon is then inflated via an inflation lumen communicating with the balloon. The inflation of the balloon causes stretching of the artery and pressing of the lesion into the artery wall to re-establish acceptable blood flow through the artery. A stent may be expanded simultaneously to provide scaffolding to the treated lesion.

The dilatation catheter is usually advanced along a guidewire that has previously been navigated to a position extending to or through the lesion to be treated. A guidewire support catheter may be advanced over a guidewire to impart stiffness to the guidewire in predetermined areas to facilitate navigation of the distal end of the guidewire to the stenosis and for crossing the stenosis. Dilatation catheters used are "over-the-wire" catheters which have a guidewire lumen over the entire length thereof or "rapid exchange" catheters which have a guidewire lumen close to the distal end only. Use of such equipment involves exchanging a catheter for a different one for a different purpose, e.g. exchanging a guidewire support catheter for a dilatation catheter or exchanging a dilatation catheter for another one, e.g. with a balloon of a different size.

Thus, it is often desirable to maintain a guidewire positioned so that its distal end remains in a wire position that is fixed relative to the occlusion, while a catheter is exchanged for a different catheter.

European patent application 0 415 332 describes the use of a trapping balloon that allows the operator to remove or exchange over the (guide)wire equipment safely and quickly. During catheter exchanges, this prevents inadvertent distal movement of guidewires. Guidewires designed to cross a stenosis are usually relatively stiff and can therefore perforate or otherwise damage a vessel of a patient easily. Maintaining the position of the distal end also ensures that the distal end is not accidentally pulled back, which would result in the need of renewed navigating to and/or traversing through the occlusion.

Trapping is achieved by first withdrawing the over-the-wire device on the guidewire several centimeters back into the guide catheter. A trapping catheter having a balloon at its distal end is arranged in the guide catheter having its balloon at or near the distal end of the guide catheter and distally beyond the partially withdrawn equipment.

The balloon is preferably not advanced out of the end of the guide catheter, since this would entail a serious risk of traumatizing the proximal coronary artery. However, visualization of the balloon catheter can be difficult and requires additional imaging and attention. Once the balloon is in the required position directly adjacent or close to the distal end of the guide catheter and distally of the partially retracted equipment, it is inflated. Inflating the balloon causes the guidewire to be clamped against an internal surface of the guide catheter and fixes its position in longitudinal direction of the guide catheter, allowing the operator to further remove the partially retracted equipment without having to take particular care of maintaining the distal end of the guidewire in an axially fixed position. Also when inserting and advancing equipment to be used next over the guidewire, the trapping balloon is left inflated, so that the newly inserted device can be advanced quickly until it abuts the balloon without reverting to fluoroscopy for monitoring its advancement through the guide catheter. The trapping balloon is then deflated and the newly inserted device can be advanced further into the coronary artery to the desired position, starting from a known position close to the distal end of the guide catheter.

SUMMARY OF THE INVENTION

It is an object of the present invention to provide a solution that allows accurate positioning of a balloon of a trapping catheter inside a guide catheter more quickly and easily.

According to the invention, this object is achieved by providing a trapping catheter for insertion into a guide catheter assembly including a guide catheter and a valve fitting mounted to a proximal end of the guide catheter, the trapping catheter including a balloon and a trapping catheter body bounding an inflation lumen extending longitudinally within the trapping catheter, the inflation lumen having a distal end opening into an internal space bounded by the balloon, wherein the trapping catheter body is provided with a stopper for abutting against an abutment at a proximal end of the guide catheter assembly so as to determine a maximum insertion depth of the trapping catheter into the guide catheter assembly.

The invention can also be embodied in a kit for insertion into a guide catheter assembly including a guide catheter and a valve fitting mounted to a proximal end of the guide catheter, the trapping catheter including a balloon and a trapping catheter body bounding an inflation lumen extending longitudinally within the trapping catheter, the inflation lumen having a distal end opening into an internal space bounded by the balloon, wherein the trapping catheter body is provided with a stopper for abutting against an abutment at a proximal end of the guide catheter assembly so as to determine a maximum insertion depth of the trapping catheter into the guide catheter assembly, wherein the stopper projects to one radial side of the trapping catheter body only, and wherein the stopper includes a curved section of the trapping catheter body, the kit including a trapping catheter for insertion into a guide catheter assembly including a guide catheter and a valve fitting mounted to a proximal end of the guide catheter, the trapping catheter including a balloon and a trapping catheter body bounding an inflation lumen extending longitudinally within the trapping balloon catheter, the inflation lumen having a distal end opening into an internal space bounded by the balloon, wherein a sheath is removably mounted to the trapping catheter body, the sheath being positioned for forming the curved portion by bending a section of the trapping catheter body adjacent to an end of the sheath or in a weakened section or interruption of the sheath.

Furthermore, the invention can be embodied in a system including a guide catheter assembly including a guide catheter and a valve fitting mounted to a proximal end of the guide catheter, and a trapping catheter according to the invention, wherein the stopper is positioned for limiting the insertion depth of the trapping catheter such that in maximally inserted condition a distal end of the trapping catheter is located within the guide catheter at less than 50 mm from a distal end of the guide catheter.

The invention can also be embodied in a method for preparing a trapping catheter prior to insertion into a guide catheter assembly including a guide catheter and a valve fitting mounted to a proximal end of the guide catheter, the guide catheter assembly having a length measured along a center line of the guide catheter and the trapping catheter including a balloon and a trapping catheter body bounding an inflation lumen extending longitudinally within the trapping balloon catheter, the inflation lumen having a distal end opening into an internal space bounded by the balloon, the method including providing the trapping catheter body with a stopper for abutting against an abutment at a proximal end of the guide catheter assembly so as to determine a maximum insertion depth of the trapping catheter such that in maximally inserted condition a distal end of the trapping catheter is located within the guide catheter at less than 50 mm from a distal end of the guide catheter.

Because the trapping catheter body is provided with a stopper for abutting against an abutment at the proximal end of the guide catheter assembly, e.g. a proximal end of a Y-connector or other fitting in a fixed position at the proximal end of the guide catheter assembly, so as to determine a maximum insertion depth of the trapping catheter into the guide catheter, the operator can insert the trapping catheter quickly into the guide catheter until the stopper abuts against the abutment, while it is ensured that the distal end of the trapping catheter is inside the guide catheter and directly adjacent to or at least close to the distal end of the guide catheter.

Particular elaborations and embodiments of the invention are set forth in the dependent claims.

Further features, effects and details of the invention appear from the detailed description and the drawings.

DETAILED DESCRIPTION

Figure 1:
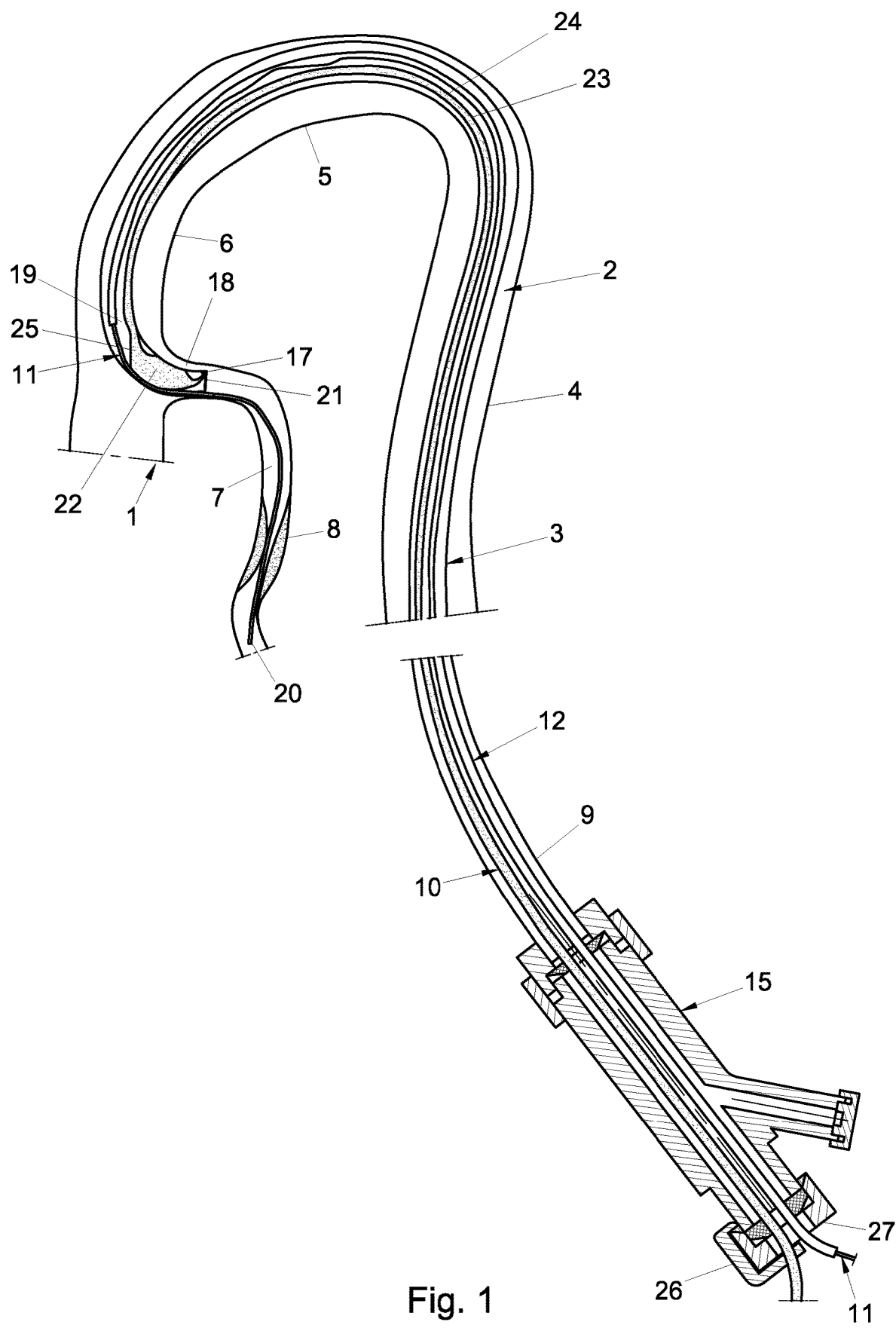
FIG. 1 is a schematic cross-sectional view of a first example of a trapping catheter and of a catheter system according to the invention.
Figure 2:
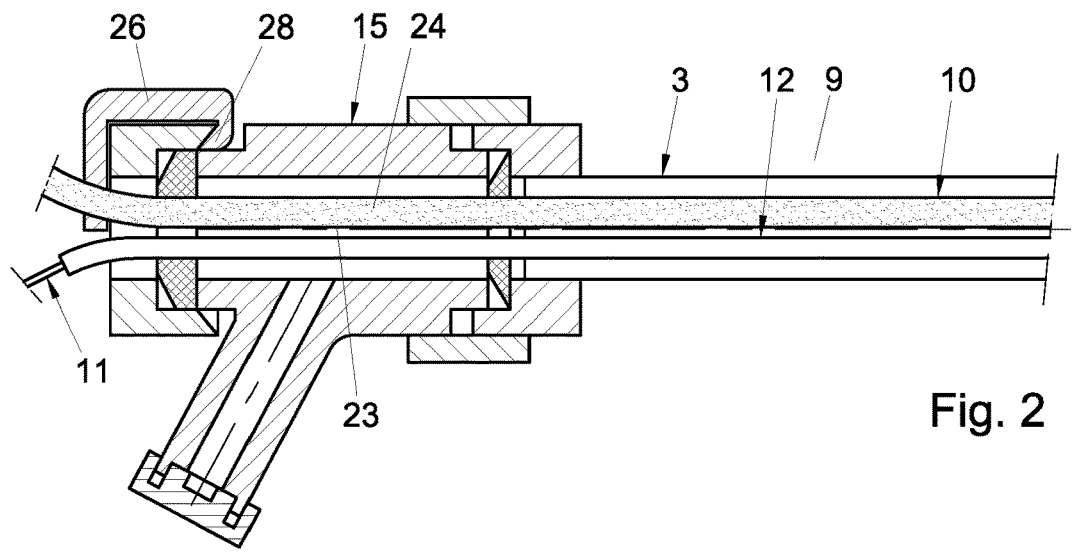
FIG. 2 is an enlarged schematic cross-sectional view of a proximal portion of the trapping catheter and of the catheter system shown in FIG. 1.

The invention is first described with reference to a first example shown in FIGS. 1 and 2. In FIG. 1, a vascular system 1 and a first example of a catheter system 2 according to the invention are shown. The guide catheter system 2 includes a guide catheter assembly 3 comprising a guide catheter 9 and a valve fitting 15 mounted to a proximal end of the guide catheter 9, and a trapping catheter 10. The guide catheter 9 has been inserted into the vascular system 1, for instance via the femoral artery (not shown). A distal portion of the vascular system 1, shown in FIG. 1, includes a descending aorta 4, an arch of aorta 5, and an ascending aorta 6. A coronary artery 7 extends from the ascending aorta 6. A stenosis 8 is formed in the coronary artery 7.

Furthermore, a guidewire 11 and a guidewire support catheter 12 extend inside the guide catheter 9. For ease of distinction in the drawings, the trapping catheter 10 has been marked with a dotted pattern. The guidewire support catheter 12 is passed over the guidewire 11. In this example, the valve fitting 15 is a Y-connector with hemostatic valves.

In use, the guide catheter 9 is inserted into the vascular system 1 at the femoral artery (not shown) and advanced until a distal end 17 of the guide catheter 9 has reached a position projecting into a mouth portion 18 of the coronary artery 7. Then, the guidewire 11 and the guidewire support catheter 12 arranged over the guidewire 11 are inserted into the guide catheter 9. Alternatively, the guidewire 11 may be inserted first followed by the guidewire support catheter 12 passing over the guidewire 11. Then, the combination of the guidewire 11 and the guidewire support catheter 12 are advanced until both extend out of the distal end 17 of the guide catheter 2. The tip of the guidewire 11 is then navigated to the stenosis 8 and across the stenosis 8. Advancement of the guidewire 11 and of the guidewire support catheter 12 may be alternated as required when flexibility or stiffness is required.

The trapping catheter 10 has a trapping catheter body 23, a balloon 22 adjacent to its distal end 21 and an inflation lumen 24 bounded by the trapping catheter body 23. The inflation lumen 24 has a distal end 25 opening into an internal space bounded by the balloon 22. In FIG. 1, the trapping catheter 10 is shown in a position inserted into the guide catheter 9 at the femoral artery (not shown) and advanced until the distal end 21 is at most flush with the distal end 17 of the guide catheter 9. To allow for tolerances, the distal end 21 of the trapping catheter 10 is preferably not advanced beyond a position slightly proximal of the distal end 21 of the guide catheter 9. The guidewire 11 is held longitudinally positioned by engaging a proximal portion of the guidewire 11 projecting out of the guide catheter 9 so that the position of the distal end 20 of the guidewire 11 relative to the stenosis 8 is maintained. The guidewire support catheter 12 to be exchanged is shown in a position retracted until its distal end 19 is proximal of the balloon 22 of the trapping catheter 10.

With the catheters 9, 10, 12 and the guidewire 11 in such positions in longitudinal direction relative to each other, the balloon 22 of the trapping catheter 10 is inflated via the lumen 24 extending through the trapping catheter body 23 of the trapping catheter 10 so that it clamps the guidewire 11 against an inner wall surface of the guide catheter 9, thereby fixing the guidewire 11 relative to the guide catheter 9 and relative to the stenosis 8.

Once the guidewire 11 has been fixed relative to the guide catheter 9 by the inflation of the balloon 22 of the trapping catheter 10, the proximal end of the guidewire 11 can be released and the dilatation catheter 12 can be pulled out of the guide catheter 9 and off of the proximal end of the guidewire 11. Since the guidewire 11 is fixed relative to the guide catheter 9, manipulating the dilatation catheter 12 off of the guidewire 11 entails very little risk of dislodgement of the distal end 20 of the guidewire 11.

Next, another equipment, such as a dilatation catheter may be placed on the proximal end of the guidewire 11 and be passed over the guidewire 11 into and through the guide catheter 9 until its distal end 19 abuts against the balloon 22 of the trapping catheter 10. Then, the proximal end of the guidewire 11 is again engaged to control its position via that proximal end and the balloon 22 of the trapping catheter 10 is deflated, thereby releasing the guidewire 11 where it was clamped between the balloon 22 of the trapping catheter 10 and the internal surface of the guide catheter 9. The newly inserted dilatation catheter 12 is then moved distally along the guidewire 11 over a short distance, starting from an accurately defined position determined by the position of a proximal end of the balloon 22 of the trapping catheter 10, towards the stenosis 8. Since the distal end of the newly inserted catheter is advanced from an accurately defined position close to the distal end 17 of the guide catheter 9, and thus close to the stenosis 8, positioning a balloon of the dilatation catheter 12 in the stenosis 8 can be carried out very quickly. After the balloon of the dilatation catheter has been positioned across the stenosis 8, the stenosis 8 can be dilated by inflating the balloon of the dilatation catheter.

During the catheter exchange procedure, the position of the guidewire 11 in its longitudinal direction is reliably maintained relative to the guide catheter 9 and relative to the stenosis 8, without requiring particular attention and holding the guidewire by hand. The new catheter can be inserted to a predetermined location near the distal end of the guide catheter 9 very quickly. Accordingly, also exposure to x-ray fluoroscopy is limited since the guidewire 11 is held stationary by the inflated balloon 22 of the trapping catheter and thus its position need not be continuously observed.

The trapping catheter body 23 of the trapping catheter 10 is provided with a stopper 26 for abutting against an abutment 27 at a proximal end 27 of the guide catheter assembly 3 so as to determine a maximum insertion depth of the trapping catheter 10 into the guide catheter 9. In this example, the abutment is formed by a proximal end 27 of a Y-connector 15 with hemostasis valves at a proximal end of the guide catheter 9. Thus, the position of the distal end 21 of the trapping catheter 10 in the guide catheter 9 is predetermined very accurately and reached by inserting the trapping catheter 10 into the guide catheter assembly 3 as far as possible until the stopper 26 hits the abutment 27, without requiring particular attention during advancement of the trapping catheter 10. In this example, the stopper 26 is clamped to the Y-connector 15 of the guide catheter assembly 3.

Preferably the maximum insertion depth of the trapping catheter 10 for use in a guide catheter 9 of a given length is such that, in maximally inserted condition, the distal end 21 of the trapping catheter 10 is located within the guide catheter 9 at less than 50 mm, or, in order of increasing preference, at less than 40, 30, 20 or 10 mm from the distal end 17 of the guide catheter 9.

Thus, accurate and quick positioning of the distal end 21 of the trapping catheter 10 is achieved by providing the trapping catheter body 23 with a stopper 26 for abutting against an abutment 27 at a proximal end of the guide catheter assembly 3 so as to determine a maximum insertion depth of the trapping catheter 10 such that, in maximally inserted condition, a distal end of the trapping catheter 10 is located within the guide catheter 9 at less than 50 mm (or less than 40, 30, 20 or 10 mm) from a distal end 17 of the guide catheter 9.

The stopper 26 has a hook 28 for hooking behind a part 29 of the valve fitting 15 of the guide catheter assembly 3, so that also the risk of inadvertent retracting movement of the trapping catheter 10, e.g. just before inflation of its balloon 22, is reduced.

In practice, guide catheters are mainly provided in lengths from balloon tip to proximal guide catheter end of 90 and 100 cm. At the proximal end of the guide catheter 9, the Y-connector, hemostasis valve or other valve fitting 15 adds to the total length of the passage through the guide catheter assembly 3. To stop advancement when the trapping balloon is positioned close to the distal end in such standard length guide catheters 9, the stopper 26 is preferably positioned for limiting the insertion depth of the trapping catheter 10 (measured from distal end to the stopper) to at most 98-103 cm or to at most 108-113 cm and more preferably to at most 101-103 cm or at most 111-113 cm.

For providing an effective and reliable clamping effect while occupying very little of the cross-sectional area of the lumen of the guide catheter 9, the balloon 22 of the trapping catheter 10 preferably has diameter of 2-3 mm or less when in expanded condition.

For providing an effective and reliable clamping effect while occupying only a small section of the guide catheter lumen when in expanded condition, the balloon 22 of the trapping catheter 10 preferably has a length of 15-35 mm.

In the present example, the stopper 26 projects further to one radial side of the trapping catheter body 23 than to an opposite side of trapping catheter body 23. Thus, obstruction of a proximal entry area of the valve fitting 15 is limited to a small area.

Figure 3:
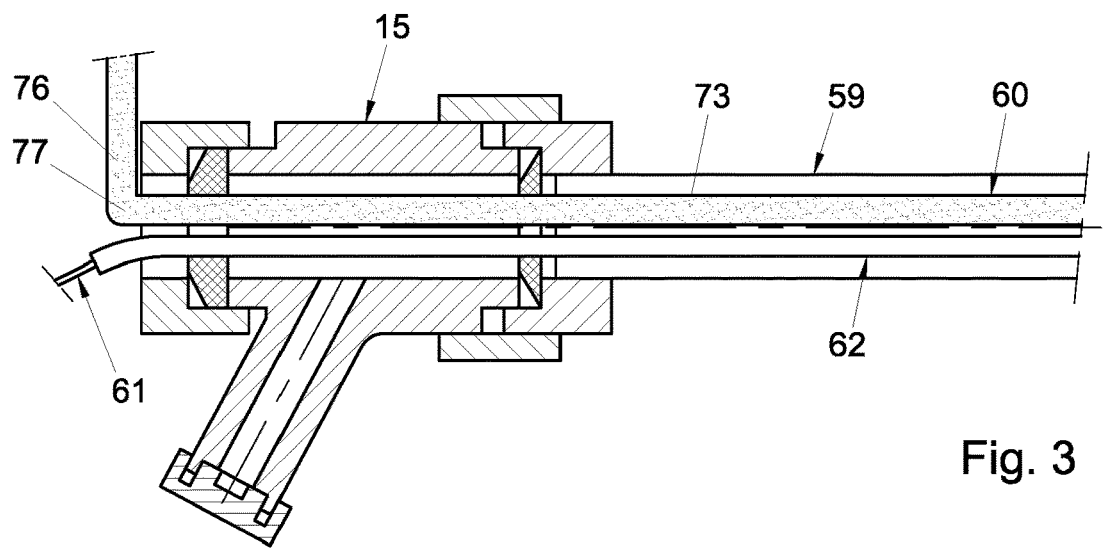
FIG. 3 is a view according to FIG. 2 of a second example of a trapping catheter and of a catheter system according to the invention.
Figure 4:
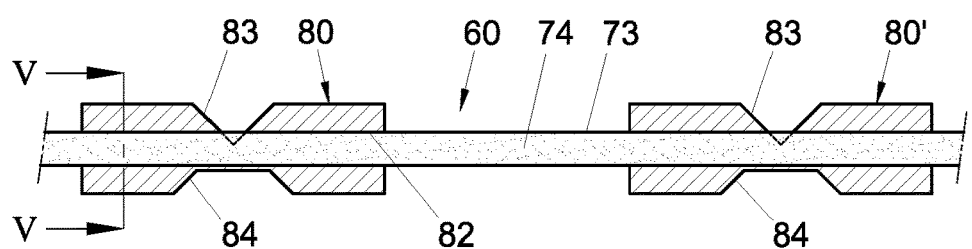
FIG. 4 is a schematic cross-sectional view of a section of a trapping catheter according to a third example of the invention.
Figure 5:
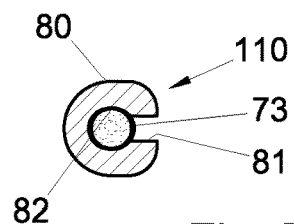
FIG. 5 is a schematic cross-sectional view along plane V-V in FIG. 4.

This feature is particularly effective if, as in the example shown in FIG. 3, the stopper 76 projects to one radial side of the trapping catheter body 73 of the trapping catheter 60 only.

In this example, a stopper 76 projecting to one radial side of the trapping catheter body 73 of the trapping catheter 10 only is obtained in a particularly simple manner by providing that the stopper 76 includes a curved section 77 of the trapping catheter body 73 of the trapping catheter 60.

For reliable abutment in an accurately determined position, the curved portion 77 preferably has a radius of less than 5 mm and more preferably of less than 3 or 4 mm and/or the curved portion 77 is curved over an angle of deflection of at least 30° and more preferably at least 45°. After the curved portion forming the stopper, the trapping catheter body may be bent in other directions, for instance bent back to a direction generally parallel to the part on the other side of the curved portion.

If the position of the stopper can be set in accordance with the length of the guide catheter, only a single version of the trapping catheter is sufficient for use in combination with guide catheters of different lengths.

This can be achieved by providing a kit for preparing a trapping catheter including a trapping catheter 60 for insertion into a guide catheter 59, the trapping catheter 60 having a balloon and a trapping catheter body 73 in which a sheath 80 is removably mounted to the trapping catheter body 73. The sheath 73 is positioned for forming the curved portion 77 by bending a section of the trapping catheter body 73 in a weakened section or an interruption of the sheath 80. The sheath may also be positioned for forming the curved portion 77 adjacent to an end of the sheath 80. Thus, the curved portion can be made particularly quickly and reliably in the right position. The sheath 80 encloses a portion of the trapping catheter body 73 adjacent to the section that is to be curved, so that it is ensured that the portions of the trapping catheter body 73 adjacent to the portion to be bent is not significantly curved after the bend has been made, and the portion to be bent can be bent easily by hand without requiring any further tools.

In the present example, a tubular member 80 in which a slot 81 is formed of a width slightly smaller than the width of a channel 82 of circular cross-section coaxial with the tubular member 80, forms the sheath. The width of the slot 81 is such that the trapping catheter body 73 of the trapping catheter 60 is held in the channel 82, but the tubular member can be removed from the trapping catheter body 73 in a direction transverse to the trapping catheter body 73 and to the tubular member 80.

The tubular member 80 has a weakening in the form of mutually opposite recesses 83, 84. A first one of these recesses 83 is of a V-shape having an intersection of opposite sidewalls approximately in line with a center line of the trapping catheter body 73 and a second one of the recesses 84 is in the form of a reduced wall thickness over approximately the maximum width of the V-shaped recess for facilitating stretching of the sheath material.

Figure 6:
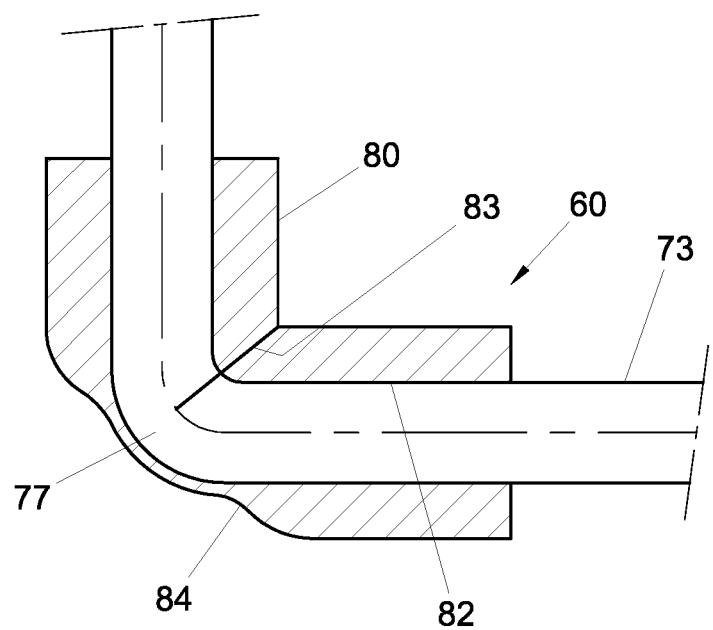
FIG. 6 is a schematic cross-sectional view of a section of the trapping catheter according to FIGS. 4 and 5 including a curved section forming a stopper.

By bending one of the sheaths 80, as is shown in FIG. 6, such that the opposite walls of the V-shaped recess are bent against each other, a curved portion 77 can easily be made in a predetermined position determined by the position in which the sheath 80 has been pre-mounted to the trapping catheter body 73 of the trapping catheter 60, by hand without needing tools and without performing any measurements or referring to small marks present on the trapping catheter body 73 of the trapping catheter 60. The sheath 80 also supports the trapping catheter body 73 evenly, so that the risk of collapsing of the internal lumen 74 of the trapping catheter body 73 is reduced. To allow for reliable and quick inflation and deflation of the balloon while occupying only a small portion of the internal cross-sectional area of the guide catheter 9 and the valve fitting 15, the internal lumen 74 of the trapping catheter body preferably has a diameter of 0.4-0.9 mm and more preferably of 0.5-0.8 mm and the trapping catheter body 73 preferably has a diameter of less than 1.2 mm and more preferably less than 1.0 mm. After bending, a curve 77 as shown in FIG. 6 is obtained and, subsequently, after the sheath 80 has been removed sideways from the trapping catheter body 73, a stopper in the form of only a sharp curve 77 in the trapping catheter body 73 as shown in FIG. 3 is obtained, so that space occupied by the trapping catheter 60 in front of the entry of the hemostasis valve is very small.

Since two of these sheaths 80 are each positioned for bending a section of the trapping catheter body 73 at a different predetermined distance from the distal end of the trapping catheter 60, the position of the stopper 76 can be determined just before use, by bending over one of the sheaths 80 that is selected in accordance with the required maximum insertion depth. The other sheath 80 is simply removed from the trapping catheter body 73 without bending at the position of that sheath. The insertion depth may also be adapted by bending at predetermined markings, which may be removable from the trapping catheter or not. This also allows adapting the maximum insertion depth of the trapping catheter to the effective length added by the valve fitting.

Several features have been described as part of the same or separate embodiments. However, it will be appreciated that the scope of the invention also includes embodiments having combinations of all or some of these features other than the specific combinations of features embodied in the examples.

The invention claimed is:

1. A trapping catheter for insertion into a guide catheter assembly, said guide catheter assembly comprising a guide catheter and a valve fitting mounted to a proximal end of the guide catheter, wherein the trapping catheter comprises:
    a balloon,
    a trapping catheter body bounding an inflation lumen extending longitudinally within the trapping catheter, the inflation lumen having a distal end opening into an internal space bounded by the balloon, and
    a stopper for abutting against an abutment at a proximal end of the guide catheter assembly so as to determine a maximum insertion depth of the trapping catheter into the guide catheter assembly,
    wherein:
    the stopper projects to one radial side of the trapping catheter body only,
    the stopper comprises a curved section of the trapping catheter body,
    said curved section of the trapping catheter body is a bent section of the trapping catheter body, and
    said curved and bent section of the trapping catheter body is bounding a correspondingly curved and bent section of said inflation lumen.

2. A trapping catheter according to claim 1, wherein the curved and bent section of the trapping catheter body has a radius of less than 5 mm.

3. A trapping catheter according to claim 1, wherein the curved and bent section of the trapping catheter body is curved over an angle of deflection of at least 45°.

4. A trapping catheter according to claim 1, wherein the stopper is positioned for limiting the maximum insertion depth of the trapping catheter to at most 98-103 cm or to at most 108-113 cm.

5. A trapping catheter according to claim 1, wherein the balloon has a diameter of 2-3 mm when in an expanded condition.

6. A trapping catheter according to claim 1, wherein the balloon has a length of 15-30 mm.

7. A kit comprising:
    an initial trapping catheter configured to be inserted into a guide catheter assembly, said guide catheter assembly comprising a guide catheter and a valve fitting mounted to a proximal end of the guide catheter, the initial trapping catheter comprising a balloon and a trapping catheter body bounding an inflation lumen extending longitudinally within the initial trapping catheter, the inflation lumen having a distal end opening into an internal space bounded by the balloon, and
    a first sheath, which is removably mounted to the trapping catheter body, the first sheath being positioned for forming a curved and bent section of the trapping catheter body by bending, at a position adjacent to an end of the first sheath or at a position in a weakened section or interruption of the first sheath, a first section of the trapping catheter body, wherein the first sheath is mounted to the trapping catheter body to facilitate forming the curved and bent section and is configured to be removed therefrom after the curved and bent section is formed, so as to transform, by said bending, said initial trapping catheter into a final trapping catheter, wherein:
    said final trapping catheter comprises a stopper for abutting against an abutment at a proximal end of the guide catheter assembly so as to determine a maximum insertion depth of the final trapping catheter into the guide catheter assembly, the stopper projects to one radial side of the trapping catheter body only, the stopper comprises said curved and bent section of the trapping catheter body, and said curved and bent section of the trapping catheter body is bounding a correspondingly curved and bent section of said inflation lumen.

8. A kit according to claim 7, further comprising a second sheath, wherein the first and second sheaths are each positioned for bending the first section and a second section, respectively, of the trapping catheter body at a different predetermined distance from a distal end of the initial trapping catheter.

9. A system comprising:

a guide catheter assembly comprising a guide catheter and a valve fitting mounted to a proximal end of the guide catheter; and a trapping catheter according to claim 1, wherein the stopper is positioned for limiting the maximum insertion depth of the trapping catheter such that, in a maximally inserted condition, a distal end of the trapping catheter is located within the guide catheter at less than 50 mm from a distal end of the guide catheter.

10. A method for preparing a trapping catheter prior to insertion into a guide catheter assembly, said guide catheter assembly comprising a guide catheter and a valve fitting mounted to a proximal end of the guide catheter, and said guide catheter assembly having a length measured along a center line of the guide catheter, and said trapping catheter comprising a balloon and a trapping catheter body bounding an inflation lumen extending longitudinally within the trapping catheter, the inflation lumen having a distal end opening into an internal space bounded by the balloon, the method comprising:

providing the trapping catheter body with a stopper for abutting against an abutment at a proximal end of the guide catheter assembly so as to determine a maximum insertion depth of the trapping catheter such that, in a maximally inserted condition, a distal end of the trapping catheter is located within the guide catheter at less than 50 mm from a distal end of the guide catheter, wherein the providing of the trapping catheter body with the stopper comprises bending a section of the trapping catheter body in such manner that:

the stopper projects to one radial side of the trapping catheter body only, the stopper comprises a curved and bent section of the trapping catheter body, and said curved and bent section of the trapping catheter body is bounding a correspondingly curved and bent section of said inflation lumen.

* * * * *